United States Patent
Wegener et al.

(10) Patent No.: US 11,969,730 B2
(45) Date of Patent: Apr. 30, 2024

(54) APPARATUS FOR SENSOR-BASED EXAMINATION OF BIOLOGICAL CELLS

(71) Applicants: FRAUNHOFER-GESELLSCHAFT ZUR FÖRDERUNG DER ANGEWANDTEN FORSCHUNG E. V., Munich (DE); UNIVERSITÄT REGENSBURG, Regensburg (DE)

(72) Inventors: Joachim Wegener, Regensburg (DE); Stefanie Michaelis, Regensburg (DE)

(73) Assignees: Universität Regensburg, Regensburg (DE); Fraunhofer-Gesellschaft zur Förderung der angewandten Forschung e.V., Munich (DE)

(*) Notice: Subject to any disclaimer, the term of this patent is extended or adjusted under 35 U.S.C. 154(b) by 752 days.

(21) Appl. No.: 16/755,114

(22) PCT Filed: Sep. 28, 2018

(86) PCT No.: PCT/EP2018/076396
§ 371 (c)(1),
(2) Date: Apr. 9, 2020

(87) PCT Pub. No.: WO2019/072588
PCT Pub. Date: Apr. 18, 2019

(65) Prior Publication Data
US 2020/0238281 A1    Jul. 30, 2020

(30) Foreign Application Priority Data
Oct. 12, 2017  (DE) .................. 10 2017 218 262.8

(51) Int. Cl.
*B01L 3/00* (2006.01)
*A01N 1/02* (2006.01)
*C12N 1/04* (2006.01)

(52) U.S. Cl.
CPC ........ *B01L 3/50851* (2013.01); *A01N 1/0268* (2013.01); *C12N 1/04* (2013.01); *B01L 2300/0645* (2013.01); *B01L 2300/0654* (2013.01); *B01L 2300/0829* (2013.01); *B01L 2300/0851* (2013.01); *B01L 2300/1894* (2013.01)

(58) Field of Classification Search
CPC ................. B01L 2300/0627; B01L 2300/0645
See application file for complete search history.

(56) References Cited

U.S. PATENT DOCUMENTS

| 5,925,511 A | 7/1999 | Fuhr et al. |
| 2005/0052646 A1* | 3/2005 | Wohlstadter .............. B01L 9/50 356/311 |
| 2010/0038247 A1* | 2/2010 | Zimmermann .. G01N 33/48728 204/547 |
| 2012/0190591 A1 | 7/2012 | Wohlstadter et al. |

FOREIGN PATENT DOCUMENTS

| DE | 4438232 A1 | 5/1996 |
| DE | 10 060 889 A1 | 6/2002 |
| DE | 102005030859 A1 | 1/2007 |
| EP | 0 347 579 A2 | 12/1989 |

OTHER PUBLICATIONS

European Patent Office, International Search Report in International Application No. PCT/EP2018/076396 (dated Jan. 2, 2019).
European Patent Office, Written Opinion in International Application No. PCT/EP2018/076396 (dated Jan. 2, 2019).
International Bureau of WIPO, International Preliminary Report on Patentability in International Application No. PCT/EP2018/076396 (dated Apr. 14, 2020).
U.S. Appl. No. 16/762,462, filed May 7, 2020.
Zaman et al., Cryopreserved cells facilitate cell-based drug discovery, *Drug Discovery Today* 12: 521-526 (2007).

* cited by examiner

*Primary Examiner* — Natalia Levkovich
(74) *Attorney, Agent, or Firm* — Leydig, Voit & Mayer, Ltd.

(57) ABSTRACT

Disclosed is an apparatus for the sensor-based examination of biological cells, comprising at least one well, wherein the at least one well has (a) an opening; (b) a planar base; (c) at least one sensor for the examination of biological cells, wherein the at least one sensor is arranged on the base of the at least one well; and (d) a medium for cryopreservation, with the medium for cryopreservation comprising biological cells and contacting a surface of the at least one sensor, wherein the medium for cryopreservation, which comprises the biological cells, is present in a frozen state.

6 Claims, 5 Drawing Sheets

APPARATUS FOR SENSOR-BASED EXAMINATION OF BIOLOGICAL CELLS

CROSS-REFERENCE TO RELATED APPLICATIONS

This patent application is the U.S. national phase of International Application No. PCT/EP2018/076396, filed on Sep. 28, 2018, which claims the benefit of German Patent Application No. 10 2017 218 262.8, filed Oct. 12, 2017, the disclosures of which are incorporated herein by reference in their entireties for all purposes.

A method for producing an apparatus for the sensor-based examination of biological cells is presented. The method comprises an equipping of at least one sterile well that has an opening and an at least regionally planar base with at least one sensor for the examination of biological cells. After the equipping of the sterile receptacle with the sensor, a liquid medium for cryopreservation containing biological cells is applied to the surface of the at least one sensor in the at least one well. The liquid medium for cryopreservation containing biological cells is subsequently frozen. An apparatus produced in this manner permits a more economical and less error-prone sensor-based examination of biological cells and their transport and storage in said apparatus up to the time of the examination. Uses of the apparatus are proposed.

The exact investigation of cell physiology and cell reactions as a response to external chemical, biological, or physical stimuli plays a decisive role in a large number of biochemical and biomedical questions. Exact knowledge of the cellular reaction is required for the evaluation of the cytotoxicity of new substances and material, in the search for active agents, or in the validation of therapeutic targets. Cell culture models are frequently used to be able to dispense with animal models in the early development phase of active agents. These in-vitro models—present for practically all body tissues—are intended to reflect the response of the respective target tissue to the applied substance under defined conditions and thus to provide first estimates of their effect in vivo. Cell lines established from tumor tissue that can be cultivated in vitro over a long period, that continuously continue to multiply, and that can be built up and stored in the long term by cryopreservation are frequently used as cell culture models.

A plurality of cell-based assays oriented on solving the problem are today available, for example, for cytotoxicity tests or active agent tests, with most of them representing so-called end-point assays. In such end-point assays, the cells are examined for a biomarker (e.g. cell structure, metabolite, and/or signal molecule) at a defined point in time after application of an external stimulus by adding detection reagents, whereby said cells are also simultaneously irreversibly destroyed, i.e. devitalized.

The disadvantage of this invasive method is that only a very restricted reproduction of the time development of a cell reaction is produced and informative details may remain hidden under certain circumstances. A very promising approach for a destruction-free and label-free analysis of cellular responses or reactions in real time is the use of physical, non-invasively working signal converters (sensors), specifically the use of substrate-integrated signal pickups (e.g. electrodes and/or optodes). In this measurement concept, the cells are cultivated directly on the surface of a physical signal converter that converts the cell response into a measurable, typically electronic, signal and thereby makes it quantifiable. The sensor surface thus simultaneously serves as a growth substrate or the cells. A direct spatial proximity of the sensor surface and the cells results herefrom, which effects a high detection sensitivity (e.g. in impedimetric measurements).

Areas of application include the screening of medicinal substances, the diagnosis of clinical samples, or the evaluation of biomaterial. Substrate-integrated signal converters have in particular made the testing of active agents considerably more comfortable, more objective, and faster, in short more efficient, in the field of high throughput screening (HTS) due to a quantitative and time-resolved data acquisition.

The use of substrate-integrated signal converters working free of labels for the examination of cellular questions has increasingly gained importance in recent years, above all due to the fact that hereby a nondestructive and continuous examination of a living, adherent cell population is possible, on the one hand, and quantitative measurement parameters can be obtained, on the other hand.

The furthest developed method in this field is the non-invasive impedimetric examination of living adherent cells on conductive planar film electrodes using AC current, also called electric cell substrate impedance sensing (ECIS). Optical or acoustic signal converters are, however, also additionally used. They include, for example, surface plasmon resonance (SPR), resonant waveguide grating" (RWG) or quartz crystal microbalance (QCM).

A direct contact between a layer of the cells and a surface of these signal converters is required for a real time analysis of a cell reaction using the above-named signal converters. In order therefore to be able to examine (e.g. impedimetrically) living cells with the aid of such substrate-integrated signal converters, the cells have to be applied as a suspension in a correspondingly defined cell density onto the sensor surface before the measurement. This preparation step is labor-intensive, time-intensive, and cost-intensive. A multiplication of the cells frozen for long-term storage (e.g. by a cell bank) and then thawed is commonly required to obtain the cell amounts required for the examination. The cells in the culture medium have to be cultivated under suitable conditions in cell culture flasks or Petri dishes for this purpose and subsequently have to be reacquired in a suitable suspension. This process can take up several days.

This process is furthermore not only labor-intensive, time-intensive, and cost-intensive, but also susceptible to error since a contamination of the cell population can easily occur in the multi-day time period that can make a provision of an examination result impossible within the prescribed time limit.

Starting from this, it was the object of the present invention to provide an apparatus that permits a less labor-intensive, less time-intensive, less cost-intensive, and less contamination-prone (simply: more economical) and additionally less error-prone and reproducible sensor-based cell examination. Furthermore, a method of its production should be provided and uses of said apparatus proposed.

The object is achieved by the features of the method and the apparatus described herein. Uses according to the invention are also described.

In accordance with the invention, a method for producing an apparatus for the sensor-based examination of biological cells is presented, comprising the steps
  a) equipping at least one sterile well, which has an opening and an at least regionally planar base, with at least one sensor for the examination of biological cells; and b) applying a liquid medium for cryopreservation, which comprises biological cells, to the surface of the at least one sensor in the at least one well, characterized in that the liquid medium for cryopreservation, which comprises biological cells, (preferably the whole well), is frozen.

The biological cells are frozen using the production method described here in a well (e.g. a well of a multiwell plate) having at least one sensor (e.g. an electrode and/or an optode). An advantage of the freezing step of the method in accordance with the invention is that the apparatus produced in this manner does not yet have to be directly used for the examination of the biological cells and is available at all times on a planned examination. The liquid medium for cryopreservation (preferably the entire well) can naturally be thawed again in a further method step. The cells contained in the well are revitalized by this measure (e.g. in that they are heated up to a temperature of 37° C.). An examination (e.g. a time-resolved examination of the formation of a cell layer) can, however, also already be started directly during the thawing process due to the contact established in the method in accordance with the invention of the cell suspension with the surface of the sensor.

A further advantage of the method in accordance with the invention is that the application of a cell suspension to a surface of the at least one sensor can in particular take place in a standardized manner with high precision and, for example, also in a sterile space. This has the significance for later examinations using the produced apparatus that the examinations are possible with a higher accuracy, better reproducibility, and less susceptibility to contamination.

In an advantageous embodiment, the freezing takes place to a temperature in a range from −200° C. to −1° C., preferably −199° C. to −10° C., particularly preferably −198° C. to −20° C., very particularly preferably −197° C. to −40° C., in particular −196° C. to −60° C., most preferably −196° C. to −80° C.

Method steps a) and/or b) can be carried out by machine, preferably using a robot configured to carry out the method step, optionally in a sterile space. A high standardization, a high reproducibility, and a small susceptibility to contamination are thus achieved.

The method in accordance with the invention can be characterized in that the at least one sensor is selected from the group consisting of electrical sensors, optical sensors, acoustic sensors, and combinations hereof, preferably selected from the group consisting of electrodes, optodes, resonant waveguide gratings, oscillating quartzes, and combinations hereof, particularly preferably selected from the group consisting of electrodes for impedimetric measurement, electrodes for potentiometric measurement, optodes for surface plasmon resonance measurement, resonant waveguides for resonant waveguide grating measurement, oscillating quartzes for quartz crystal microbalance measurement, and combinations hereof.

The at least one sensor used in the method can furthermore comprise or consist of a material that is selected from the group consisting of metals, semiconductors, electrically conductive polymers, and combinations hereof, with the material preferably being selected from the group consisting of precious metals, mixed oxide semiconductors, polymers having conjugated double bonds, and combinations hereof, particularly preferably selected from the group consisting of gold, indium-tin oxide, polypyrrole, polythiophene, and combinations and derivatives thereof.

The sensor used in the method can comprise or consist of at least two layers that are preferably arranged in a coplanar manner in the well.

The sensor used in the method can furthermore be produced photolithographically. It is in particular advantageous for microscopic examinations for the at least one sensor used in the method to be transparent for light of a wavelength in the range from 300 nm to 700 nm.

The at least one sensor used in the method can be arranged on the base of the at least one well, preferably on a planar region of the base. The at least one sensor is particularly preferably at least partly integrated in the base of the at least one well. The at least one sensor can furthermore be arranged through the base of the at least one well. In a preferred embodiment, the at least one sensor is arranged through the base of the at least one well and contacts a measurement device for detecting a signal of the sensor on a side disposed opposite the opening of the well. An electrical, optical, and/or acoustic interface is hereby provided on this side of the well by which information can be simply communicated from the at least one sensor to a measurement device.

The at least one well used in the method can comprise or consist of a material that is selected from the group consisting of metals, plastics, glasses, and combinations hereof, preferably selected from the group consisting of plastics that do not show any crack formation on a cooling to a temperature in the range from −200° C. to −10° C., particularly preferably plastics selected from the group consisting of polycarbonate, polyethylene terephthalate, polystyrene, and mixtures and combinations hereof. The material can furthermore be transparent for light having a wavelength in the range from 300 nm to 700 nm. The material can furthermore be sterilized by a treatment with plasma, particularly preferably by a treatment with air plasma and/or argon plasma, in particular for a time period of 20 to 60 sec. The material can furthermore be hydrophilized by an argon plasma at least regionally, preferably at the base and/or at at least one side wall of the well. The hydrophilization has the advantage that less cell-compatible materials can also be converted at least at parts of their surface into cell-compatible materials.

In the method, the well can optionally be provided at the base with an elevated portion, optionally a ring-shaped elevated portion that is connected to the base in a fluid-tight manner or that is designed monolithically with the base of the well. The elevated portion has a height that is less than the height of the well, preferably a height that is less than 80%, less than 60%, less than 40%, less than 20%, or less than 10%, of the height of the well. The elevated portion furthermore bounds a surface at the base of the well that is smaller than the total surface of the base, preferably a surface that is less than 80%, less than 60%, less than 40%, less than 20%, or less than 10% of the surface of the base.

The well used in the method can be a well of a multiwell plate and the multiwell can include at least two wells, preferably having the features of the at least one well, preferably at least 6, at least 12, at least 24, at least 48, or at least 96 wells (optionally having the features of the at least one well), with the cell suspension particularly preferably being pipetted into at least two of the wells, in particular in all of the wells of the apparatus.

The medium for cryopreservation used in the method can include an aqueous buffer solution, preferably selected from the group consisting of cell culture medium, blood serum, aqueous solutions of at least one buffer that demonstrates a buffer action in the pH range from 6 to 8, and mixtures hereof, with the cell culture medium and/or the aqueous solution of the at least one buffer optionally including blood serum, and with the aqueous buffer solution preferably having a pH in a range from 7.0 to 7.4. The medium for cryopreservation can furthermore include a cryoprotective substance that is preferably selected from the group consisting of DMSO, glycerin, trehalose, and mixtures thereof. The (suspended) biological cells included in the medium for cryopreservation can be selected from the group consisting of animal cells, vegetable cells, microorganisms, and mixtures thereof, preferably selected from the group consisting of biological cells from a tissue of an animal organism, particularly preferably selected from the group consisting of keratinocytes, renal cells, astrocytes, glial cells, cardiomyocytes, epithelial cells, endothelial cells, stem cells, neurons, and combinations hereof, very particularly preferably selected from the group consisting of rat kidney cells, HaCaT cells, U373 cells, and combinations hereof.

The freezing of the well can take place in a freezer, with the freezing preferably being carried out at a cooling rate in the region of 0.1 to 10 K per minute, particularly preferably 0.2 to 5 K/min., very particularly preferably 0.5 to 2 K/min., in particular 1 K/min. An apparatus for the sensor-based examination of biological cells is furthermore provided in accordance with the invention. The apparatus comprises at least one well, with the at least one well comprising
 a) an opening;
 b) an at least regionally planar base;
 c) at least one sensor for the examination of biological cells; and
 d) a medium for cryopreservation, with the medium for cryopreservation comprising biological cells and contacting a surface of the at least one sensor,
 characterized in that the medium for cryopreservation, which comprises the biological cells, (preferably the entire well or the entire apparatus) being present in a frozen state.

The apparatus in accordance with the invention permits a less labor-intensive, less time-intensive, less cost-intensive, less contamination-prone (i.e. a more economical) sensor-based cell examination less falsified by system-induced causes (i.e. a reproducible sensor-based cell examination). The cell examination using the apparatus in accordance with the invention is associated with lower costs since expensive infrastructure (e.g. expensive equipment and expensive materials for the cell culture and the cell harvest, trained staff) is no longer required for preparatory work up to the carrying out of the examination.

Different cell types can furthermore be simultaneously examined with a minimal effort by the apparatus in accordance with the invention without the different cell types having to be cultivated directly before the examination.

The apparatus in accordance with the invention furthermore reduces the risk that the cells are contaminated before the examination since the cells are already on the surface of the sensor and no longer have to be applied (e.g. pipetted) onto the sensor surface briefly before the examination.

Since the pipetting of the cell suspension onto the surface of the at least one sensor customary in the prior art and varying from person to person in accuracy is omitted, an examination of biological cells using the apparatus in accordance with the invention has fewer systematic measurement errors. The apparatus in accordance with the invention furthermore permits an examination of identical cells of a batch so that no batch-to-batch variations occur and cell culture-induced (changes in the phenotype and/or a dedifferentiation, transdifferentiation, differentiation of the cells and user-induced fluctuations in the provision of the biological cells are omitted, whereby the spread of the measurement results obtained is considerably reduced.

The apparatus in accordance with the invention finally permits a simpler planning capability and logistics of the cell examinations since thawing adapted to requirements is possible in respectively required quantities.

In an advantageous embodiment, the freezing takes place to a temperature in a range from −200° C. to −1° C., preferably −199° C. to −10° C., particularly preferably −198° C. to −20° C., very particularly preferably −197° C. to −40° C., in particular −196° C. to −60° C., most preferably −196° C. to −80° C.

The at least one sensor of the apparatus can be selected from the group consisting of electrical sensors, optical sensors, acoustic sensors, and combinations hereof, preferably selected from the group consisting of electrodes, optodes, resonant waveguide gratings, oscillating quartzes, and combinations hereof, particularly preferably selected from the group consisting of electrodes for impedimetric measurement, electrodes for potentiometric measurement, optodes for surface plasmon resonance measurement, resonant waveguides for resonant waveguide grating measurement, oscillating quartzes for quartz crystal microbalance measurement, and combinations hereof.

The at least one sensor of the apparatus can furthermore comprise or consist of a material that is selected from the group consisting of metals, semiconductors, electrically conductive polymers, and combinations hereof, with the material preferably being selected from the group consisting of precious metals, mixed oxide semiconductors, polymers having conjugated double bonds, and combinations hereof, particularly preferably selected from the group consisting of gold, indium-tin oxide, polypyrrole, polythiophene, and combinations and derivatives thereof.

In addition, the at least one sensor of the apparatus can comprise or consist of at least two layers that are preferably arranged in a coplanar manner in the at least one well.

The sensor can furthermore be produced photolithographically. It is in particular advantageous for microscopic examinations for the at least one sensor to be transparent for light of a wavelength in the range from 300 nm to 700 nm.

In a preferred embodiment of the apparatus, the at least one sensor of the apparatus is arranged on the base of the at least one well, preferably on a planar region of the base. The at least one sensor can particularly preferably be at least partly integrated in the base of the at least one well. The at least one sensor can furthermore be arranged through the base of the at least one well. In a particularly preferred embodiment, the at least one sensor is arranged through the base of the at least one well and contacts a measurement device for detecting a signal of the sensor on a side disposed opposite the opening of the well.

The at least one well of the apparatus can comprise or consist of a material that is selected from the group consisting of metals, plastics, glasses, and combinations hereof, preferably selected from the group consisting of plastics that do not show any crack formation on a cooling to a temperature in the range from −200° C. to −10° C., particularly preferably plastics selected from the group consisting of polycarbonate, polyethylene terephthalate, polystyrene, and mixtures and combinations hereof. The material can furthermore be transparent for light having a wavelength in the range from 300 nm to 700 nm. The material can furthermore be sterilized, particularly preferably by a treatment with plasma, preferably by a treatment with air plasma and/or argon plasma, in particular for a time period of 20 to 60 sec. The material can furthermore be hydrophilized by an argon plasma at least regionally, preferably at the base and/or at at least one side wall of the well. The hydrophilization has the advantage that less cell-compatible materials can also be converted at least at parts of their surface into cell-compatible materials.

In a preferred embodiment, the well optionally has an elevated portion, optionally a ring-shaped elevated portion, at the base of the apparatus that is connected to the base in a fluid-tight manner or that is designed monolithically with the base of the well. The elevated portion has a height that is less than the height of the well, preferably a height that is less than 80%, less than 60%, less than 40%, less than 20%, or less than 10%, of the height of the well. The elevated portion furthermore bounds a surface at the base of the well that is smaller than the total surface of the base, preferably a surface that is less than 80%, less than 60%, less than 40%, less than 20%, or less than 10%, of the surface of the base.

In a preferred embodiment, the well is a well of a multiwell plate and the multiwell plate includes at least two wells, preferably having the features of the at least one well. The multiwell plate preferably has at least 6, at least 12, at least 24, at least 48, or at least 96 wells (optionally having the features of the at least one well), with the (frozen) cell suspension particularly preferably being pipetted into at least two of the wells, in particular in all of the wells of the apparatus.

The medium for cryopreservation can include an aqueous buffer solution (in the frozen state), preferably selected from the group consisting of cell culture medium, blood serum, aqueous solution of at least one buffer that demonstrates a buffer action in the pH range from 6 to 8, and mixtures hereof, with the cell culture medium and/or the aqueous solution of the at least one buffer optionally including blood serum, and with the aqueous buffer solution preferably having a pH in a range from 7.0 to 7.4. The medium for cryopreservation can furthermore include a cryoprotective substance (in the frozen state) that is preferably selected from the group consisting of DMSO, glycerin, trehalose, and mixtures thereof. The medium for cryopreservation can furthermore include biological cells (in the frozen state) that are selected from the group consisting of animal cells, vegetable cells, microorganisms, and mixtures thereof, preferably selected from the group consisting of biological cells from a tissue of an animal organism, particularly preferably selected from the group consisting of keratinocytes, renal cells, astrocytes, glial cells, cardiomyocytes, epithelial cells, endothelial cells, stem cells, neurons, and combinations hereof, very particularly preferably selected from the group consisting of rat kidney cells, HaCaT cells, U373 cells, and combinations hereof.

The apparatus in accordance with the invention is preferably producible or produced using the method in accordance with the invention.

The use of the apparatus in accordance with the invention for an identification and/or analysis of at least one active agent is furthermore proposed. The apparatus in accordance with the invention can also be used for an identification and/or analysis of at least one toxic substance. The apparatus in accordance with the invention can furthermore be used for an examination of biocompatibility. The apparatus in accordance with the invention can furthermore be used for an examination of at least one differentiation procedure of the cells and/or an examination of a metabolic activity of the cells. The apparatus can furthermore be used for an identification of the cells and/or for the determination of their quality. The apparatus and/or the at least one well of the apparatus are in particular heated to a temperature in the range from 1° to 40° C., preferably 36° C. to 38° C., prior to the measurement.

The subject matter in accordance with the invention will be explained in more detail with reference to the following Figures and examples without intending to restrict it to the specific embodiments shown here.

Figure 1:
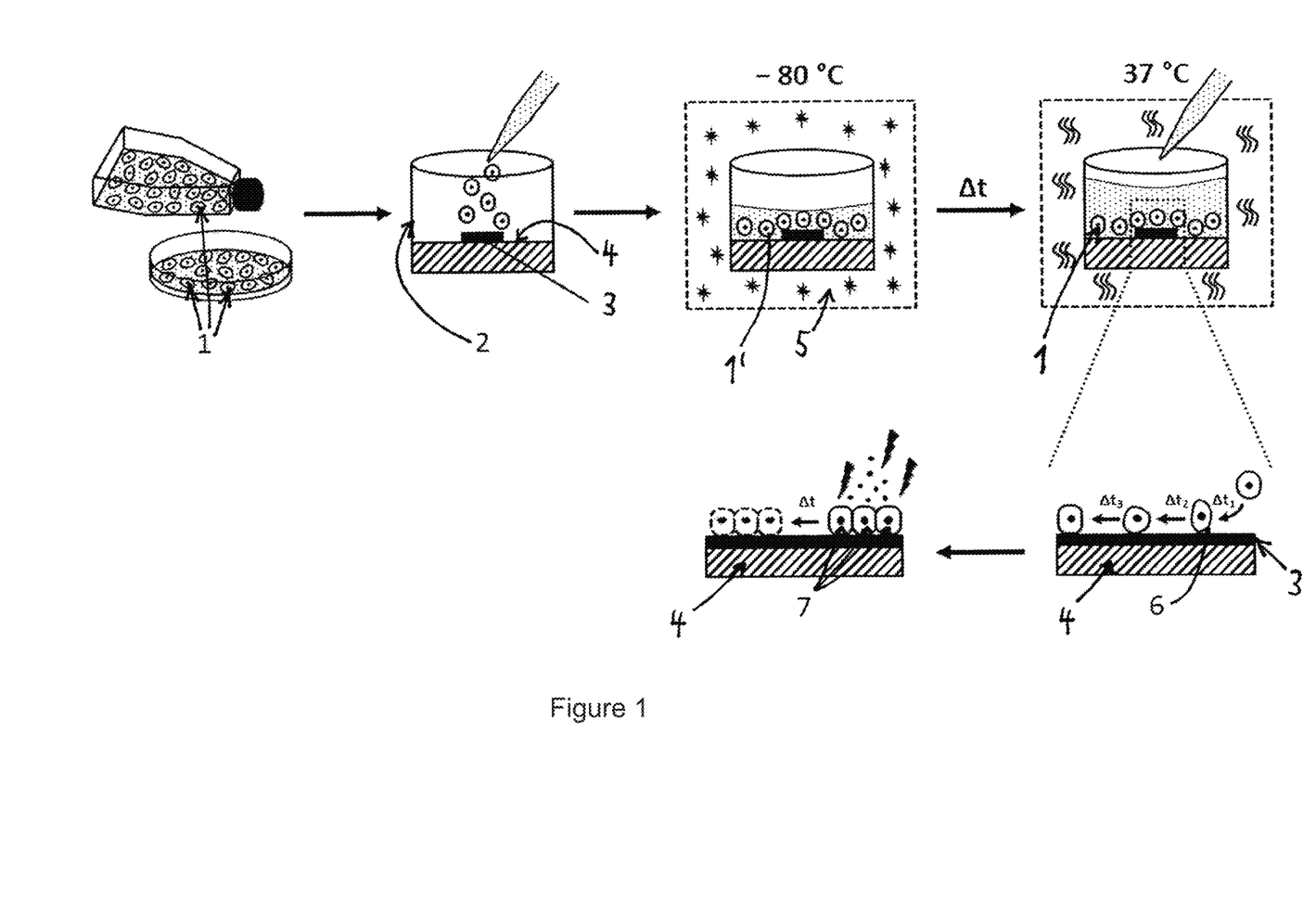

FIG. 1 illustrates a method of freezing or cryopreserving suspended cells 1 in a plurality of wells of an apparatus in accordance with the invention. The cells 1 to be frozen are first located in a preparatory culture. A suspension of these cells 1 in freezing medium is pipetted into each well 2 having a sensor 3 (here: an electrode for an impedimetric measurement). The apparatus in accordance with the invention is frozen, preferably by a cooling of the cell suspension at a cooling rate of 1° C./min to a storage temperature of −80° C. The frozen cells 1' are stored in a freezer 5 at −80° C. The cells are thawed to form a liquid cell suspension at 37° C. after a specific time. This can be done directly by an addition of medium preheated to 37° C. After deposition of the cells due to gravity, adhesion 6 of the cells 1 at the surface of the sensor 3 and of the base 4 of the well 2 takes place. Stimulants can now be added to the formed cell layer 7 and a cell reaction can be analyzed via the sensor 3.

Figure 2:
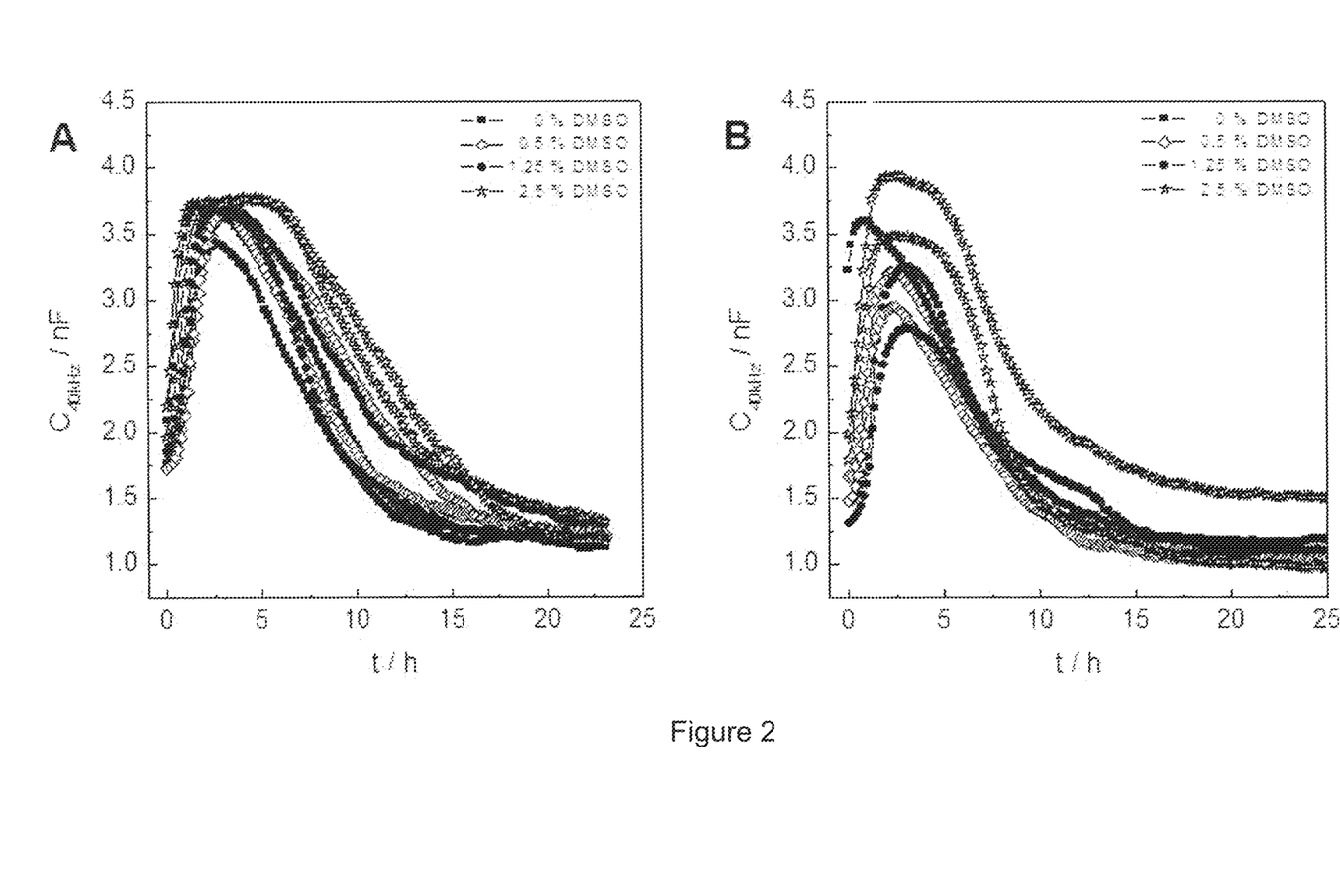

FIG. 2 shows the time development of the capacitance C (f=40 kHz) during the adhesion of suspended HaCaT cells on the sensor surface (here: an electrode for an impedimetric measurement) of an apparatus in accordance with the invention. FIG. 2A shows the result for cells after cryopreservation over 5 weeks at −80° C. and after the revitalization using culture medium at the time t=0 min. FIG. 2B shows the result for cells from a cell suspension that comes from a non-cryopreserved permanent culture. The cell density on the sensor surface is 450,000 cells/cm$^2$ (T=37° C.) in both cases. The decrease in the capacitance reflects the increasing electrode coverage.

Figure 3:
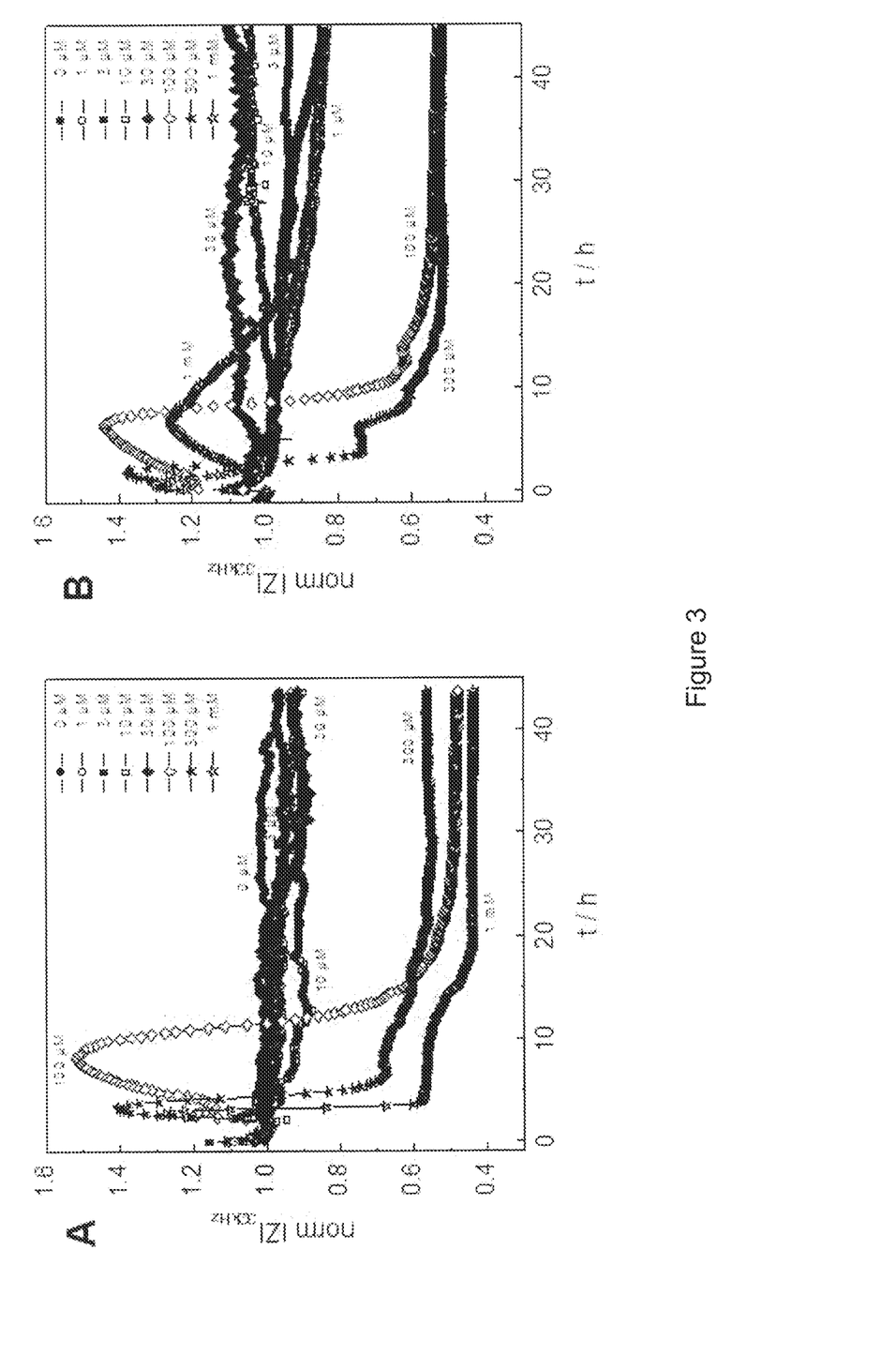

FIG. 3 shows the time development of the standardized impedance norm. IZI at 32 kHz for confluent HaCaT cells that were incubated (cytotoxicity assay) at the time t=0 h with increasing concentrations of $CdCl_2$. FIG. 3A shows a revitalized cell layer after cryopreservation over 7 days at −80° C. and FIG. 3B shows a fresh cell suspension of the same density (450,000 cells /cm$^2$ from a permanent culture. $CdCl_2$ was applied 24 h after revitalization or cell seeding respectively (T=37° C.).

Figure 4:
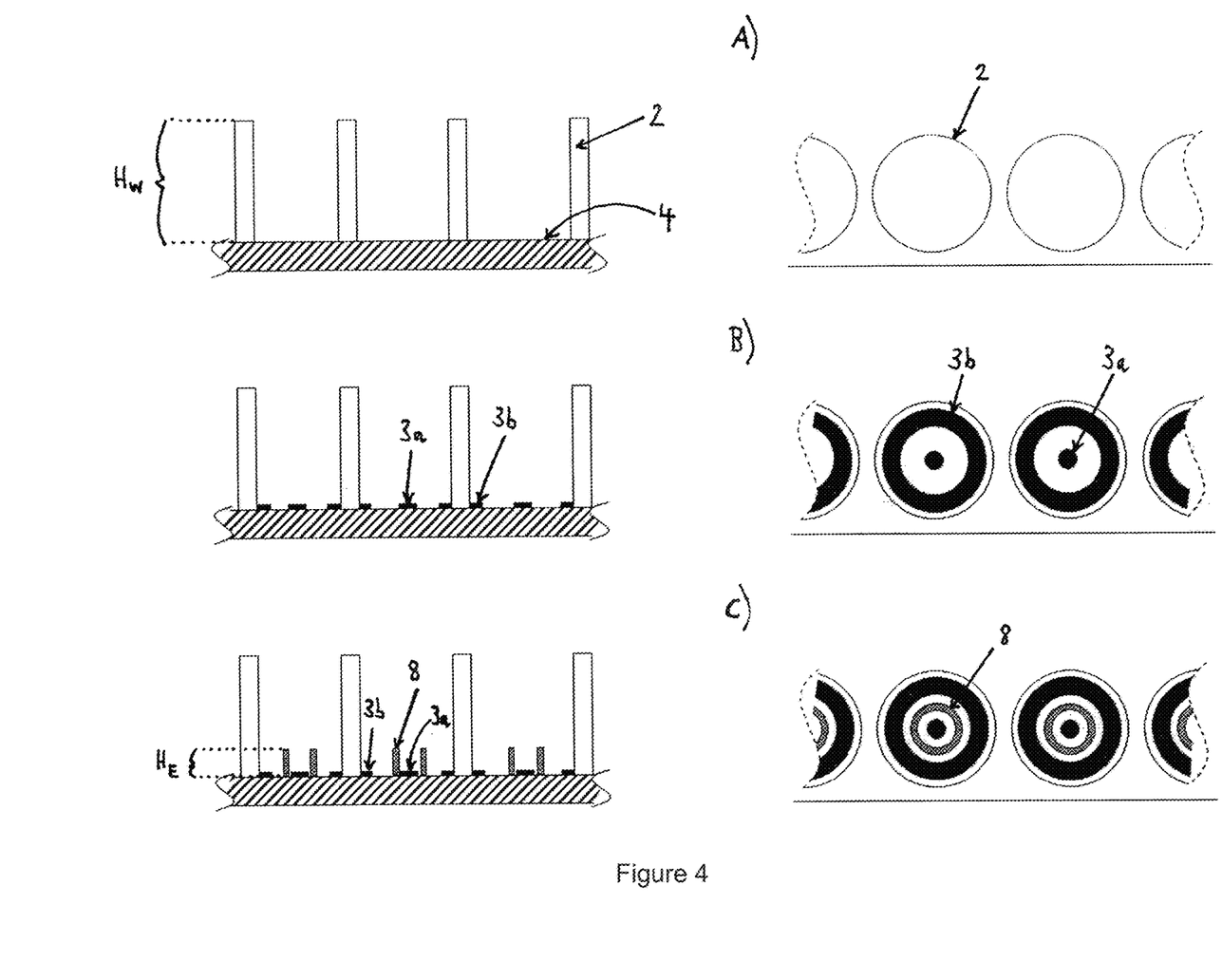

FIG. 4 first only shows a conventional multiwell plate in FIG. 4A. Two variants of an apparatus in accordance with the invention are shown in FIGS. 4B and 4B in which a first part 3a of a sensor is positioned centrally at the base 4 of the well 2 (of a multiwell plate) (here: a punctiform working electrode of gold) and a second part 3b of a sensor is arranged at the margin of the base 4 of the well 2 (here: a ring-shaped counter-electrode of gold). In both variants, the wall of the well 2 has a specific height $H_W$ and bounds the volume of the well 2. In the variant shown in FIG. 4C, the well 2 additionally comprises an elevated portion 8 at the base of the well 2 (here: a ring of e.g. plastic) that is arranged between the counter-electrode 3b and the working electrode 3a at the base 4 of the well 2 and that is connected to the base 5 of the well 2 in a fluid-tight manner. The elevated portion 8 has a smaller height $H_E$ than the height $H_W$ of the wall of the well 2. The variant shown in FIG. 4C permits a compartmentalization of the cells in the cryopreservation medium within the well 2 ("cryocompartmentalization") and thus also allows a reliable wetting of the surface of the first part 3a of the sensor with very small volumes of the cell suspension to be frozen. The small requirement for suspension volume above all represents a large economic advantage in the examination of cost-intensive cells. The counter-electrode 3b is furthermore protected from damage that can occur due to the cell suspension or the cells.

Figure 5:
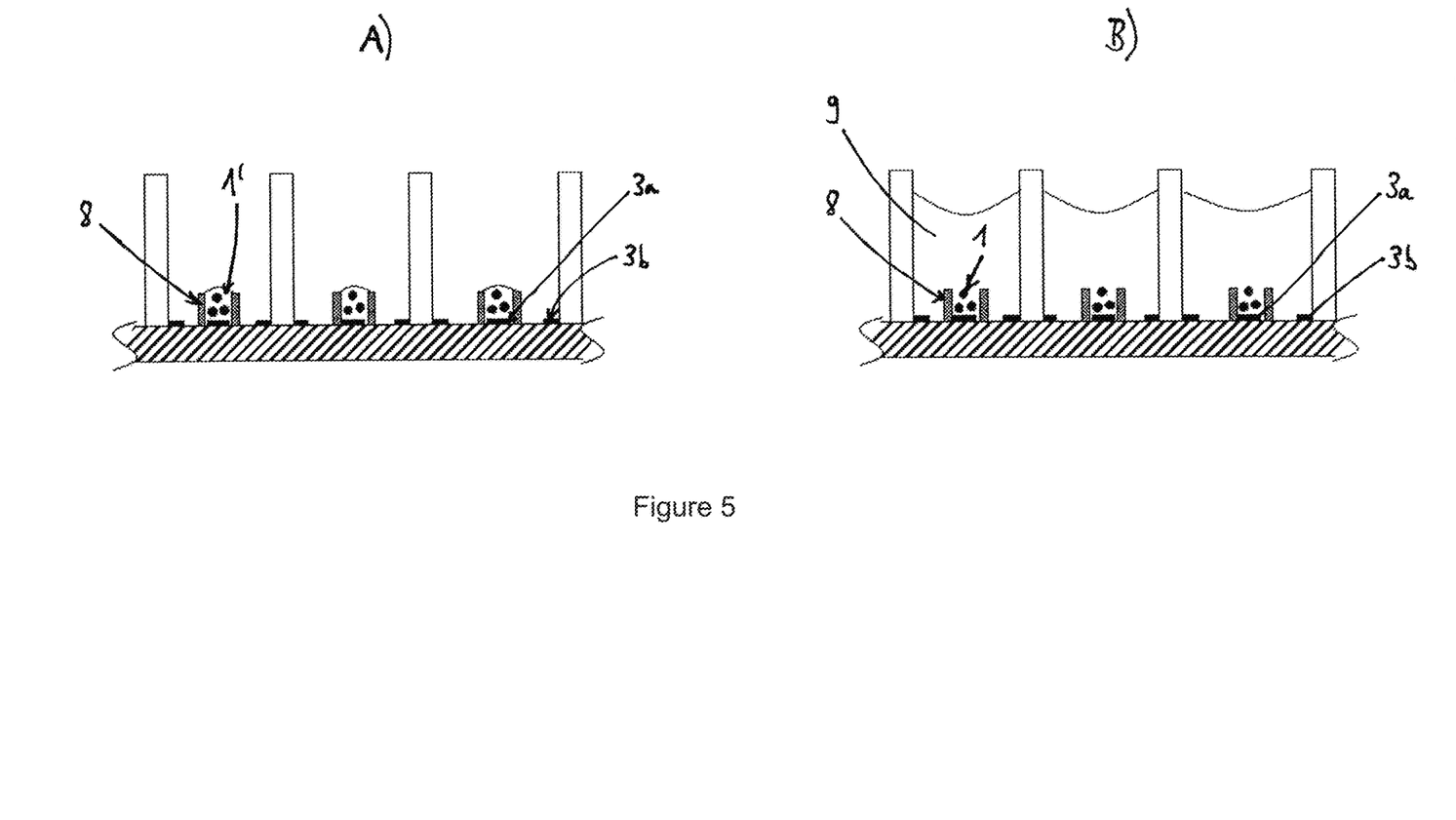

FIG. 5 illustrates the use of the variant of the apparatus in accordance with the invention shown in FIG. 4C. The frozen apparatus shown in FIG. 5A only has the frozen suspension of biological cells 1' in the partial volume of the well 2 bounded by the elevated portion 8. It is achieved by a fast filling of the well 2 with heated (e.g. raised to a temperature of 37° C.) culture medium 9 that the frozen cell suspension 1' not only thaws quickly, but also locally remains in the volume bounded by the elevated portion 8. This state during thawing is shown in FIG. 5B. The remaining of the cell suspension in the volume bounded by the elevated portion 8 has the effect that a cell layer is only formed on the part of the base 4 of the well 2 bounded by the elevated portion 8 and the counter-electrode 3b remains free of a cell layer. This can have a positive effect on the quality of the measurement signal depending on the sensor 3a, 3b used.

EXAMPLE 1

Production and use of an Apparatus in Accordance with the Invention

Cells growing adherently in a cell culture flask or in a Petri dish are first received in a precisely set cell density in a small volume of a special freezing medium (contains a cryoprotective substance such as DMSO or glycerin) after an enzymatic release (e.g. using a trypsin solution) from their cell culture flask or from their Petri dish.

This cell suspension is subsequently filled into the wells of the apparatus in accordance with the invention, here the wells of a multiwell plate. Gold film electrodes are located as a sensor on the base of the wells.

The filled multiwell plate is frozen and stored in a deep freezer at −80° C.

When required, the cells can be thawed and used for an experiment. The multiwell plate is removed from the deep freezer for this purpose. Culture medium is pipetted into the thawed cell suspension to revitalize the cells so that the freezing medium is diluted by a multiple.

Since the measurements are carried out with living cells, all the following experiments have to take place in an incubator at a constant temperature of 37° C.

After connecting the sensor array to corresponding measurement electronics, the adhesion of the still suspended cells to the surface of the signal converter (here an electrode) can be tracked with time resolution so that a monitoring of the cell viability and of the formation of an intact cell layer on the sensor/electrode surface already takes place during this first phase after the thawing (quality control/viability detection of the thawed cells).

After adhesion to the surface of the signal converter, the cells are accessible to further cell-physiological examinations such as cytotoxicity screenings, active agent screening, and/or differentiation studies.

Alternatively, the data recording can also only begin after cell adhesion and cell spreading.

EXAMPLE 2

Survival Rate of Cells Stored and Thawed in the Apparatus in Accordance with the Invention The thawing of the apparatus in accordance with the invention takes place with the loss of living cells typical for a cryopreservation. The survival rate was determined by the classical viability assay "PrestoBlue". Based on the PrestoBlue viability assay, the following survival rates were able to be demonstrated for different cell lines 48 h after thawing.

| Cells | Survival rate |
|---|---|
| Normal rat kidney cells | (86 ± 3)% |
| HaCaT cells | (89 ± 9)% |
| U373 cells | (92 ± 4)% |

This confirms the non-invasive character of the cryopreservation of living cells on the sensor surface of the apparatus in accordance with the invention and thus validates the general functionality of the apparatus in accordance with the invention.

EXAMPLE 3

Comparison of the Viability of Cells Stored and Thawed in the Apparatus in Accordance with the Invention with Newly Cultivated Cells It was found that the cells stored on the sensor surface by cryopreservation are fully viable after thawing and take up their normal physiological processes again so that they do not differ physiologically from freshly seeded cells from a continuously growing culture.

To check the viability state of the frozen cells and then thawed again, the kinetics of the adhesion of human skin cells (keratinocytes, HaCaT cells) to the electrode surface (of gold) after a cryopreservation of more than five weeks at −80° C. were tracked directly after thawing (revitalization) with time resolution via an impedimetric readout (see FIG. 2A). The time development of the capacitance C of the total system at a measurement frequency of 40 kHz is in linear dependence on the occupation of the electrode with adherent cells and thus reflects the progressing process of the cell adhesion.

The time development of the capacitance for newly seeded cells of the same density from a continuously growing cell culture of the same passage number (batch) (see FIG. 2B) that was not cryopreserved is set against this for comparison.

The culture medium is modeled on the freezing medium after revitalizing the cells in the chemical composition. Variable DMSO contents were selected to freeze the cells to be able to directly optimize the freezing medium for the respective cell line.

The similarity of the capacitance developments after thawing of cryopreserved cells, respectively after seeding of new cells of the same density, demonstrates that cryopreserved cells adhere similarly fast to the electrode surface and form a dense cell layer.

FIG. 2A furthermore clearly shows for HaCaT cells that these cells can also be frozen without cryoprotective, but that a proportion of 10% by volume DMSO in the freezing medium also has no negative effect on the cell viability after thawing.

The provision of frozen cells in wells having integrated signal converters thus permits the quantitative online documentation of cell-physiological processes at any desired time after the thawing of the cells and the adhesion of the cells to the electrode surface.

The data shown in the following document that the cells are not only viable, but also unchangeably sensitive to chemical stimuli.

FIG. 3 shows a comparison of a impedimetric toxicity study with HaCaT cells that were, on the one hand, frozen in suspension on the sensor array at −80° C. for 7 days prior to the experiment and were subsequently thawed (see FIG. 3A) and that were, on the other hand, newly seeded onto the sensor array from a continuous culture (see FIG. 3B).

The cell density was identical in both cases. Increasing concentrations of the heavy metal salt $CdCl_2$ served as the chemical model toxin. The assay was carried out 24 h after thawing, respectively seeding.

The cell response to the addition of $CdCl_2$ is documented with reference to the time profile of the normed impedance at a measurement frequency of 32 kHz. The initially high impedance of the cell-covered electrodes decreases in dependence on the dosage as a consequence of the onset of toxification of the cells. The time developments, also highly characteristic of the impedance after the addition of $CdCl_2$ to the confluent cell layers for every concentration of $CdCl_2$ for the cryopreserved cells are indistinguishably similar to those of the newly seeded cells.

The similar toxicity profiles of both populations document a similar chemosensitivity of newly seeded cells and cells frozen on the sensor surface.

A further embodiment, not shown in further detail here, is the cryopreservation of beating heart muscles (cardiomyocytes) in multiwell plates with integrated impedance electrodes. The cells can be tracked and analyzed in their contraction patterns after adhesion to the electrode surface by time-resolved impedance measurements.

REFERENCE NUMERAL LIST

1: suspended biological cells
1': frozen biological cells
2: well (e.g. of a multiwell plate)
3: sensor
3a: first part of the sensor
3b: second part of the sensor
4: base of the well
5: freezer
6: adhesion of the suspended cells
7: cell layer
8: elevated portion at the base (e.g. a ring)
9: culture medium (e.g. heated to 37° C.)
Hw: height of the wall of the well
$H_E$: height of the elevated portion at the base of the well

The invention claimed is:

1. An apparatus for the sensor-based examination of biological cells, comprising at least one well, wherein the at least one well has
    (a) an opening;
    (b) a planar base;
    (c) at least one sensor for the examination of biological cells, wherein the at least one sensor is arranged on the base of the at least one well; and
    (d) a medium for cryopreservation, with the medium for cryopreservation comprising biological cells and contacting a surface of the at least one sensor, wherein the medium for cryopreservation, which comprises the biological cells, is present in a frozen state.

2. The apparatus of claim 1, wherein the at least one sensor
    (i) is selected from the group consisting of electrical sensors, optical sensors, acoustic sensors, and combinations thereof; and/or
    (ii) comprises a material that is selected from the group consisting of metals, semiconductors, electrically conductive polymers, and combinations thereof.

3. The apparatus of claim 1, wherein the at least one well is constructed from a material that
    (i) is selected from the group consisting of metals, plastics, and combinations thereof; and/or
    (ii) is transparent for light with a wavelength in the range from 300 nm to 700 nm; and/or
    (iii) is sterilized; and/or
    (iv) is hydrophilized by an argon plasma at least regionally.

4. The apparatus of claim 1, wherein the base of the at least one well is provided with an elevated portion that is connected to the base of the at least one well in a fluid-tight manner, with the elevated portion
    (i) having a height that is less than a height of the at least one well and/or
    (ii) bounds a surface at the base of the at least one well that is smaller than the total surface of the base of the at least one well.

5. The apparatus of claim 1, wherein the at least one well is at least one well of a multiwell plate and the multiwell plate includes at least one further well.

6. The apparatus of claim 1, wherein the medium for cryopreservation includes
    (i) an aqueous buffer solution; and/or
    (ii) a cryoprotective substance selected from the group consisting of DMSO, glycerin, trehalose, and mixtures thereof.

* * * * *